(12) United States Patent
Gossen

(10) Patent No.: US 11,541,063 B2
(45) Date of Patent: Jan. 3, 2023

(54) COMPOSITIONS AND PRODUCTS FOR USE IN THE TREATMENT OF BONE FRACTURES AND DEFECTS

(71) Applicant: OSTEO-PHARMA B.V., Oss (NL)

(72) Inventor: Jan Albert Gossen, Oss (NL)

(73) Assignee: Osteo-Pharma B.V., Oss (NL)

( * ) Notice: Subject to any disclaimer, the term of this patent is extended or adjusted under 35 U.S.C. 154(b) by 60 days.

(21) Appl. No.: 16/679,044

(22) Filed: Nov. 8, 2019

(65) Prior Publication Data

US 2020/0069707 A1  Mar. 5, 2020

Related U.S. Application Data

(62) Division of application No. 15/320,060, filed as application No. PCT/NL2015/050490 on Jul. 3, 2015, now abandoned.

(30) Foreign Application Priority Data

Jul. 4, 2014  (EP) ................... 14175801

(51) Int. Cl.
| | | |
|---|---|---|
| *A61K 31/663* | (2006.01) | |
| *A61K 9/00* | (2006.01) | |
| *A61K 31/568* | (2006.01) | |
| *A61K 45/06* | (2006.01) | |
| *A61K 9/70* | (2006.01) | |
| *A61L 27/14* | (2006.01) | |
| *A61L 27/54* | (2006.01) | |
| *A61L 27/58* | (2006.01) | |

(52) U.S. Cl.
CPC .......... *A61K 31/663* (2013.01); *A61K 9/0024* (2013.01); *A61K 9/703* (2013.01); *A61K 31/568* (2013.01); *A61K 45/06* (2013.01); *A61L 27/14* (2013.01); *A61L 27/54* (2013.01); *A61L 27/58* (2013.01); *A61L 2300/45* (2013.01); *A61L 2430/02* (2013.01)

(58) Field of Classification Search
CPC .............. A61K 2300/00; A61K 31/663; A61K 9/0024; A61K 9/703; A61K 31/568; A61K 45/06; A61L 27/14; A61L 27/54; A61L 27/58; A61L 2300/45; A61L 2430/02; A61P 19/00; A61P 19/08; A61F 2/28; A61F 2002/2817; A61F 2002/2835
See application file for complete search history.

(56) References Cited

U.S. PATENT DOCUMENTS

| | | | | |
|---|---|---|---|---|
| 3,602,225 A ‡ | 8/1971 | Wielicki | ............ | A61F 13/15252 264/193 |
| 4,160,452 A ‡ | 7/1979 | Theeuwes | ............ | A61F 9/0017 424/427 |
| 4,351,337 A ‡ | 9/1982 | Sidman | ................ | A61K 9/0024 424/424 |
| 6,120,491 A ‡ | 9/2000 | Kohn | ................... | C08G 69/44 528/176 |
| 6,309,669 B1 ‡ | 10/2001 | Setterstrom | .......... | A61K 9/1647 424/486 |
| 6,815,469 B1 ‡ | 11/2004 | Voelkel | ................ | A61K 9/0024 523/105 |
| 8,475,811 B2 * | 7/2013 | Yang | ..................... | A61K 6/853 424/400 |
| 2006/0173009 A1 * | 8/2006 | Kanoh | .................... | A61P 19/08 514/248 |
| 2010/0168188 A1 ‡ | 7/2010 | Greenlee | ............. | C07D 231/54 514/359 |
| 2010/0197636 A1 | 8/2010 | Bouler et al. | | |
| 2010/0247607 A1 * | 9/2010 | Ashton | .................. | A61P 19/10 424/426 |
| 2012/0101593 A1 ‡ | 4/2012 | D'Agostino | ......... | A61K 9/0024 623/23 |

FOREIGN PATENT DOCUMENTS

| | | | | |
|---|---|---|---|---|
| DE | 19908753 | ‡ | 10/2003 | |
| EP | 2067494 | ‡ | 6/2009 | |
| WO | WO-98/23274 | | 6/1998 | |
| WO | WO-9823274 A1 | ‡ | 6/1998 | ............. A61K 31/66 |
| WO | WO 9823274 A1 | ‡ | 6/1998 | ............. A61K 31/66 |
| WO | WO-199823274 | ‡ | 6/1998 | |
| WO | WO-2000/064516 | | 11/2000 | |
| WO | WO-200064516 | ‡ | 11/2000 | |
| WO | WO-2009/121935 | | 10/2009 | |
| WO | WO-2009121935 | ‡ | 10/2009 | |

OTHER PUBLICATIONS

Posadowska, U. R. S. Z. U. L. A., et al. "Preparation and characterization of drug delivery carriers for local administration of sodium alendronate." Engineering of Biomaterials 16 (2013). (Year: 2013).*
Long, K. (2006). Controlled release of alendronate from polymeric films (T). University of British Columbia. Retrieved from https://open.library.ubc.ca/collections/ubctheses/831/items/1.0092541. (Year: 2006).*
Reinholz, Gregory G., et al. "Bisphosphonates directly regulate cell proliferation, differentiation, and gene expression in human osteoblasts." Cancer research 60.21 (2000): 6001-6007. (Year: 2000).*
Chen et al., Testosterone inhibits osteoclast formation stimulated by parathyroid hormone through androgen receptor, FEBS Letters, vol. 491, Issues 1-2, pp. 91-93. (Year: 2001).*
Zhang et al., Effect of Ginsenoside From The Stem and Leaf on Different Skeletal Sites of Osteoporotic Rats Induced by D-Galactose, Chin. J. Osteoporos, Mar. 2013, vol. 19, No. 3.‡

(Continued)

*Primary Examiner* — Abigail Vanhorn
(74) *Attorney, Agent, or Firm* — Banner & Witcoff, Ltd.

(57) ABSTRACT

The invention relates to methods for treatment of bone fractures and defects, in particular to method that accelerate fracture healing, and to compositions, injectable in situ depot forming formulations and patches comprising at least one biodegradable polymer, an androgen receptor agonist and a bisphosphonate or pharmaceutically acceptable salt thereof for use in such methods.

15 Claims, 1 Drawing Sheet

(56) References Cited

OTHER PUBLICATIONS

Jiang, et al., Influence of Alendronate on Osteoblast Proliferation of Rat Steroblasts, Orthop. J. Chin., vol. 13, No. 12, Jun. 2005.‡
Shimon, I., et al., "Alendronate for osteoporosis in men with androgen-repleted hypogonadism," Osteoporos Int (2005) 16: 1591-1596.‡
Fahrleitner-Pammer, A., et al., "Testosterone replacement in combination with bisphosphonate therapy in male cardiac transplant patients exerts additional benefits on bone mass: A 5-year prospective study," Abstracts/Bone 44 (2009) S339-S450.‡
Goswami and Naik, "Natural gums and its pharmaceutical application", J Scientific Innov Res 3(1): 112-121 (2014) (Year: 2014).‡
Fahrleitner-Pammer et al., "Testosterone replacement in combination with bisphosphonate therapy in male cardiac transplant patients exerts additional benefits on bone mass: A 5-year prospective study", Bone 44: 5339-5450 (2009). (Year: 2009).‡
Cremers et al., "Pharmacokinetics/pharmacodynamics of bisphosphonates: use for optimization of intermittent therapy for osteoporosis", Clin Pharmacokinet 44: 551-570 (2005) (Year: 2005).‡
Risedronate Sodium—PubChem, 2018 (Year: 2018).‡
Alendronate Sodium—PubChem, 2018 (Year: 2018).‡
Shuwisitkul, Biodegradable Implants with Different Drug Release Profiles, Thesis, pp. 1-160. (Year: 2011).‡
Einhorn, "Can an anti-fracture agent heal fractures", Clin Cases Mineral Bone Metab 6: 251-253 (2010) (Year: 2010).‡
Amanat et al., "A single systemic dose of pamidronate imprives bone mineral content and accelerates restoration of strength in a rat model of fracture repair", J Orthopaedic Res 23: 1029-1034 (2005) (Year: 2005).‡
Alendronate Sodium—PubChem, 2018 at section 3.4.1 (Year: 2018).‡
Fahrleitner-Pammer et al., "Testosterone replacement in combination with bisphosphonate therapy in male cardiac transplant patients exerts additional benefits on bone mass:&nbsp; A 5-year prospective study", Bone 44: 5339-5450 (2009), Abstract at P450 (Year: 2009).‡
Cremers et al., "Pharmacokinetics/pharmacodynamics of bisphosphonates:&nbsp; use for optimization of intermittent therapy for osteoporosis", Clin Pharmacokinet 44: 551-570 (2005) (Year: 2005).‡
Alendronate Sodium—PubChem, at section 3.4.1 (2018).
Amanat et al., "A single systemic dose of pamidronate improves bone mineral content and accelerates restoration of strength in a rat model of fracture repair", J Orthopaedic Res (2005) 23:1029-1034.
Cheng et al., "Testosterone delivered with a scaffold is as effective as bone morphologic protein-2 in promoting the repair of critical-size segmental defect of femoral bone in mice", PloS One (2013) 8(8):e70234.
Cremers et al., "Pharmacokinetics/pharmacodynamics of bisphosphonates use for optimization of intermittent therapy for osteoporosis", Clin Pharmacokinet (2005) 44:551-570.
Einhorn, "Can an anti-fracture agent heal fractures", Clin Cases Mineral Bone Metab (2010) 6:251-253.
Fahrleitner-Pammer et al., "Testosterone replacement in combination with bisphosphonate therapy in male cardiac transplant patients exerts additional benefits on bone mass: A 5-year prospective study", Bone (2009) 44:S339-S450 Abstract at P450.
Goswami and Naik, "Natural gums and its pharmaceutical application", J Scientific Innov Res (2014) 3(1):112-121.
Jiang et al., "Influence of Alendronate on Osteoblast Proliferation of Rat Steroblasts", Orthop. J. Chin., vol. 13, No. 12, 2005.
Risedronate Sodium—PubChem, 2018.
Shuwisitkui, Biodegradable Implants with Different Drug Release Profiles, Thesis (2011) pp. 1-160.

\* cited by examiner
‡ imported from a related application

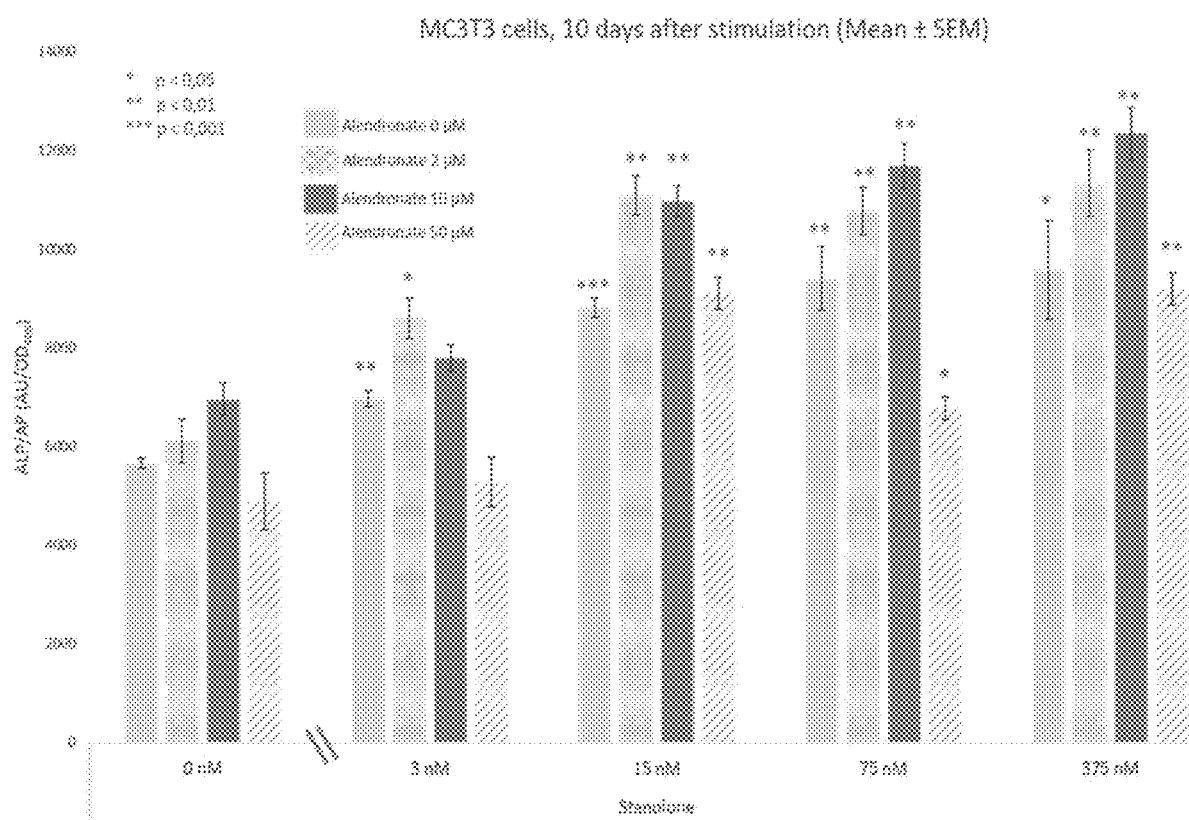

COMPOSITIONS AND PRODUCTS FOR USE IN THE TREATMENT OF BONE FRACTURES AND DEFECTS

CROSS-REFERENCE TO RELATED APPLICATIONS

This application is a divisional of U.S. Ser. No. 15/320,060 having an international filing date of 3 Jul. 2015, which is the national phase of PCT application PCT/NL2015/050490 having an international filing date of 3 Jul. 2015, which claims benefit of European patent application No. 14175801.1 filed 4 Jul. 2014. The contents of the above patent applications are incorporated by reference herein in their entirety.

FIELD OF THE INVENTION

The invention relates to methods for treatment of bone fractures and/or bone defects, in particular to a method to accelerate fracture healing, and to compositions, injectable in situ depot forming formulations and patches for use in such methods. The invention also relates to bone fillers, medical devices and bone implants for use in such method. The invention in particular relates to short term local treatment of fractures and defects.

BACKGROUND OF THE INVENTION

A bone fracture is a complete or incomplete break in a bone. A bone fracture can be the result of high force impact or stress, or trivial injury as a result of certain medical conditions that weaken the bones. A bone fracture is referred to as traumatic fracture, i.e. a fracture that is caused by trauma, such as fractures caused by a fall or an accident, such as a traffic accident. A fracture of a bone which is the result of an underlying disease that weakens the bone, such as osteoporosis, Paget's disease or bone cancer, is referred to as a pathological fracture. A fracture is called simple (or closed) when the overlying skin is not broken and the bone is not exposed to the air. If the skin is broken and the bone is exposed the fracture is called a compound (or open) fracture.

Fracture healing is divided into three, partly overlapping phases, an inflammatory phase, a repair phase, and a remodeling phase. During the inflammatory phase, a hematoma develops within the site of fracture within the first few hours and days following fracture Inflammatory cells including macrophages, monocytes, lymphocytes, and polymorphonuclear cells, and fibroblasts infiltrate the bone, which results in the formation of granulation tissue, growth of vascular tissue, and migration of mesenchymal cells. During the repair phase, the hematoma is removed from the fracture site and substituted with granulation tissue which leads to the formation of a soft callus at the repair site. Differentiation of osteoblastic and chondryocytic cells occurs during this phase. The soft callus is remodeled into hard callus, and new bone is formed by osteogenic cells. Fracture healing is completed during the remodeling phase, wherein the bone is restored to its original shape, structure, and mechanical strength, via organized osteoblastic/osteoclastic activity. Remodeling occurs slowly and takes months to years to complete.

Bone defects are gaps or voids in bone that may be the result of a variety of causes, such as trauma, e.g. accidents and/or fractures, or removal of bone segments by surgery, for instance of malignant bone tumors. Current treatment of bone defects mainly entails the use of bone fillers such as bone cement and demineralized bone matrix. Bone cement is further used for adherence of implants to existing bone. A main disadvantage of the use of bone fillers is the lack of or limited remodeling or replacement by new bone and consequent inability to adhere to existing bone. A further important disadvantage of bone cement, as well as bone implants, is aseptic loosening. Aseptic loosening is the development of voids around a prosthetic filler and/or implant, in particular at the site where bone and implant/filler are adjacent to each other. Aseptic loosening can be the result of inadequate initial fixation, loss of fixation over time or loss of fixation caused by particle-induced osteolysis around an implant. Aseptic loosing may also result from voids at the bone-cement/implant interface. Such voids are always present after implant introduction and are typically filled by mainly fibrous tissue containing only a few cells and blood vessels. Repeated mechanical stress, such as during movement, may induces trauma at the interface and eventually loosening of the bone-implant interface. Aseptic loosening may even necessitate premature replacement of an implant.

Currently only limited effective treatments are available that aid in bone fracture healing, in particularly that accelerate healing of traumatic and/or complicated fractures in the early stages after fracture has occurred.

Bisphosphonates have an inhibitory effect on osteoclastic bone resorption. They have been used in diseases with increased bone resorption such as osteoporosis, Paget's disease and bone cancer. The activity of bisphosphonates is thought to prevent bone loss and improve bone strength by inhibiting osteoclast-mediated bone resorption. Bisphosphonates are however only found to lower the risk of fracture, but to have no function in healing of fractured bones or generating bone tissue. In fact, treatment with bisphosphonates during bone healing after bone fracture is often thought to be detrimental because osteoclasts are necessary for remodeling callus into bone in the remodeling phase during fracture healing.

In a number of animal studies bisphosphonates have been shown to have a positive effect on callus size and bone mineral content. However, this never resulted in increased bone strength or accelerated healing confirming the indispensable role of osteoclast in callus remodeling. Einhorn, TA (2010) provides an overview of pharmacological treatment of bone fractures in animal models. Bisphosphonates are reported to result in increased callus size, but also in reduced callus remodeling and/or bone formation after long term treatment of fractures. Short time studies are described that report increased callus size and increased bone mineral content after systemic treatment with bisphosphonates. Local application of a bisphosphonate also increased callus size and bone mineral content, but this did not translate into increased callus strength. The author concludes that local application of bisphosphonates may have on inhibitory effect on the fracture healing process and that long-term bisphosphonate treatment may be a valuable therapy.

Bisphosphonates have also been used in coatings of screws implanted in bone, see e.g. Wermelin K et al. (2008) and Aspenberg P et al. (2008). Wermelin K et al. (2008) report that the fixation of titanium implants in bone is improved by bisphosphonate coating. Aspenberg P et al. (2008) use a combination of bisphosphonates and parathyroid hormone (PTH), an 84 amino acid polypeptide that increases serum calcium levels. Continuous PTH exposure stimulates osteoclast activity, while intermittent exposure stimulates osteoblasts and the overall effect in osteoporosis is that PTH has a positive effect on bone formation. Aspenberg P et al. (2008) report that PTH and bisphosphonates as a coating on stainless steel screws have an additive effect on fixation of the screw in bone.

A recent meta-analysis by Xue et al. (2014) of randomized controlled trials confirms the results obtained in animal studies. Xue et al. report that their meta-analysis revealed that bisphosphonates do not have an effect on short time and long time bone healing.

Testosterone is an anabolic agent affecting the activity of osteoblasts and increasing osteogenesis. Clinical trials have been conducted for the use of testosterone to prevent osteoporosis or prevent further bone loss after osteoporosis has been diagnosed in men who have low testosterone levels, where it resulted in a small increases in bone density. However, due to adverse effects on the liver and cardiovascular system, testosterone has not been approved for such applications. The effect of testosterone on traumatic bone fracture in mice is described by Cheng et al. (2013). Local application of testosterone in a scaffold induced callus formation and increased the number of osteoclasts in the callus. No effects on callus remodeling and strength of the resulting bone are reported.

Combined treatment with a bisphosphonate and an androgen is described in WO 98/23274. However, this document does not address treatment of bone fractures or bone defects. Instead, it relates to the treatment of diseases involving bone resorption, such as osteoporosis and Paget's disease, the pathological processes of which differ to a large extent from bone damage and repair after e.g. fracture or defects. The documents further does not relate to the local treatment of bone.

During the process of bone healing, patients are seriously hampered in their activity and may experience a substantial effect on quality of life. Patients for instance experience difficulties in performing regular daily activities and limitations in the ability to work, leading to limited productivity, loss of independence, reduced self esteem, and, possibly chronic, pain. As mentioned above, the total healing process take several months to years to complete. There is thus a need for a medical treatment that aids in healing of bone fracture. Such medical treatment preferably accelerates bone healing after fracture so that the total time of fracture to heal is reduced. There is further a need for improved treatment of bone defects, which addresses the disadvantages associated with the use of bone fillers and bone implants discussed above. In addition there is a need for a medical treatment of bone fracture or defect that avoids adverse effects of bisphosphonates, including the suppression of bone turnover at a location other than the site of fracture discussed above but also e.g. hypocalcemia and upper GI adverse effects after oral administration, and of anabolic drugs such as adverse effect on the liver or other organs, the reproductive system, the cardiovascular system and serum lipid profile, and on behavior, but that at the same time provides a sustained treatment of the fracture site.

SUMMARY OF THE INVENTION

It is an object of the present invention to provide a method of treatment of bone fracture which aids the fracture healing process, including pathological, traumatic and complicated fractures. It is a further object of the present invention to provide a method of treatment of bone defects which stimulates bone formation and inhibits bone resorption in order to improve attachment of e.g. bone implants and bone fillers to existing bone.

The invention therefor provides a method of treating a bone fracture or defect in a patient, preferably a human patient, comprising administering to a site of fracture or defect a patch or injectable in situ depot forming formulation comprising at least one biodegradable polymer and a combination of an androgen receptor agonist and a bisphosphonate or pharmaceutically acceptable salt thereof and/or comprising introducing a bone filler comprising at least one biodegradable polymer and a combination of an androgen receptor agonist and a bisphosphonate or pharmaceutically acceptable salt thereof, or a bone filler, a medical device or a bone implant provided with a coating comprising at least one biodegradable polymer and a combination of an androgen receptor agonist and a bisphosphonate or pharmaceutically acceptable salt thereof to or into a site of bone fracture or bone defect.

In a further aspect the invention provides a composition comprising an androgen receptor agonist and a bisphosphonate or pharmaceutically acceptable salt thereof for use in a method of treatment of a bone fracture or a bone defect. Said method preferably comprises applying an injectable in situ forming depot formulation or a patch comprising at least one biodegradable polymer and a combination of an androgen receptor agonist and a bisphosphonate or pharmaceutically acceptable salt thereof to a site of fracture or defect and/or introducing a bone filler comprising at least one biodegradable polymer and a combination of an androgen receptor agonist and a bisphosphonate or pharmaceutically acceptable salt thereof, or a bone filler, a medical device or a bone implant provided with a coating comprising at least one biodegradable polymer and a combination of an androgen receptor agonist and a bisphosphonate or pharmaceutically acceptable salt thereof to or into a site of bone fracture or bone defect.

In a still further aspect the invention provides a use of an androgen receptor agonist and a bisphosphonate or pharmaceutically acceptable salt thereof for the preparation of a medicament for the treatment of a bone fracture or a bone defect. Said treatment preferably comprises applying an injectable in situ forming depot formulation or a patch comprising at least one biodegradable polymer and a combination of an androgen receptor agonist and a bisphosphonate or pharmaceutically acceptable salt thereof to a site of fracture or defect and/or introducing a bone filler comprising at least one biodegradable polymer and a combination of an androgen receptor agonist and a bisphosphonate or pharmaceutically acceptable salt thereof, or a bone filler, a medical device or a bone implant provided with a coating comprising at least one biodegradable polymer and a combination of an androgen receptor agonist and a bisphosphonate or pharmaceutically acceptable salt thereof to or into a site of bone fracture or bone defect.

In a still further aspect the invention provides a composition comprising at least one biodegradable polymer, an androgen receptor agonist and a bisphosphonate or pharmaceutically acceptable salt thereof.

In a still further aspect the invention provides injectable in situ forming depot formulations, patches, coatings and bone fillers comprising a composition comprising at least one biodegradable polymer, an androgen receptor agonist and a bisphosphonate or pharmaceutically acceptable salt thereof.

DETAILED DESCRIPTION OF THE INVENTION

The invention relates to bone repair, in particular to the treatment of bone fractures or bone defects, more in particular to the local treatment of bone fractures or bone defects. The compositions, patches and formulations are therefore preferably for local administration to bone and/or local treatment of bone. The term "bone fracture" as used herein includes both complete and incomplete fracture and both traumatic fracture and pathological fractures. A "complete fracture" refers to a break over the entire diameter of a bone, whereas an "incomplete break" refers to a partial fracture which does not spans the entire diameter of a bone. "Traumatic fracture" as used herein refers to a fracture that is caused by trauma, such as fractures caused by a fall or an accident, such as a traffic accident. "Pathological fracture" as used herein refers to a fracture of a bone which is the result of an underlying disease that weakens the bone, such as osteoporosis or bone cancer. The term "bone defect" refers to a gap or void in bone. Examples of factors that may underlie the development of such void or gaps include, but are not limited to trauma, such as trauma caused by a fall or an accident, (vertebral) compression fracture, bone cysts, cancer induced defects, e.g. bone tumors including both primary bone tumors and metastases of e.g. other types or cancer such as breast, prostate, lung or kidney cancer or multiple myeloma, and the surgical removal of such tumors. Such bone defect are typically treated by introducing bone void fillers or bone implants into the site of the defect.

Without wishing to be bound by theory, it is believed that the activity of the combined treatment with an androgen receptor agonist, preferably testosterone or a derivative thereof, and a bisphosphonate or pharmaceutically acceptable salt thereof is at least in part the result of a synergistic effect of the two active compounds, in particular of the anabolic effect of the androgen receptor agonist and the anti-catabolic effect of the bisphosphonate when administered locally at the site of a bone fracture or defect. As demonstrated in the FIGURE, the combination of a bisphosphonate and an androgen receptor agonist results in a substantial and significant increase in activity of osteoblast cells as compared to a bisphosphonate alone. Bisphosphonates inhibit osteoclast-mediated bone resorption by inhibiting the intracellular mevalonate pathway which results in impaired membrane localization so the osteoclast signaling molecules guanosine triphosphatases or by being metabolized to nonhydrolyzable, analogs of ATP, both leading to osteoclast apoptosis. Androgen receptor agonists affect bone development by enhancing osteoblast proliferation and differentiation via binding to the androgen receptor. The combined local effects of an androgen receptor agonist, preferably testosterone, and a bisphosphonate are thought to act synergistically in preventing bone loss and improving bone strength, in particular in the early stages, up to 4 months, after fracturing.

The compositions, formulations and patches of the invention comprise a combination of two active compounds, an androgen receptor agonist and a bisphosphonate or pharmaceutically acceptable salt thereof. "Androgen receptor agonist" as used herein refers to any natural or synthetic compound that binds to and activates the androgen receptor (AR). Preferred androgen receptor agonists are anabolic steroids, more preferred testosterone or a derivative thereof. The term "anabolic steroid" is well understood in the art and refers to a class of steroid hormones related to testosterone. Anabolic steroids are reviewed in Kicman AT, British Journal of Pharmacology (2008) 154, 502-521. "Testosterone or a derivative thereof" as used herein refers to testosterone, testosterone esters, testosterone precursors, testosterone metabolites and testosterone analogues. Examples of suitable derivatives useful in the compositions and methods of the present invention are testosterone esters testosterone cypionate, testosterone decanoate, testosterone enanthate, testosterone isocaproate, testosterone phenylpropionate, testosterone propionate and testosterone undecanoate; testosterone precursors androstenedione, 4-androstenedione, 5-androstenedione, androstenediol, 5-androstenediol, 4-androstenediol and dehydroepiandrosterone; testosterone metabolites dihydrotestosterone and etiocholanolone; testosterone analogues methyl testosterone, androsterone, epiandrosterone, nandrolone, 17 α-ethyl testosterone and fluoxymesterone. The testosterone or derivative is therefore preferably selected from the group consisting of testosterone, testosterone cypionate, testosterone decanoate, testosterone enanthate, testosterone isocaproate, testosterone phenylpropionate, testosterone propionate, testosterone undecanoate, androstenedione, 4-androstenedione, 5-androstenedione, androstenediol, 5-androstenediol, 4-androstenediol, dehydroepiandrosterone, nandrolone, dihydrotestosterone, etiocholanolone, methyl testosterone, androsterone, epiandrosterone, 17 α-ethyl testosterone and fluoxymesterone. More preferably the testosterone or derivative is selected from the group consisting of testosterone, nandrolone and dihydrotestosterone. Most preferably the androgen receptor agonist is testosterone.

The amount of the androgen receptor agonist, preferably an anabolic steroid, more preferably testosterone or a derivative thereof, that is locally applied to the site of a bone fracture or defect in accordance with the present invention is preferably such that no systemic effects of the androgen receptor agonist occur and, consequently, adverse effects of androgen receptor agonists such as those on the liver or other organs, the reproductive system, the cardiovascular system and serum lipid profile are avoided. This means that the dosage of the androgen receptor agonist preferably does not result in serum levels that exceed four times, preferably twice, the average concentration of serum testosterone in humans. Preferred amounts of testosterone or a derivative locally applied in accordance with the present invention, preferably of testosterone, are therefore between 1 μg and 10 mg, more preferably between 5 μg and 5 mg, more preferably between 15 μg and 2.5 mg, more preferably between 20 μg and 1.5 mg, most preferably about 50 μg. This amount is preferably present in a patch or injectable depot forming formulation according to the invention. The amount of the androgen receptor agonist, preferably an anabolic steroid, more preferably testosterone or a derivative thereof, that is locally applied to the site of a bone fracture or defect as a coating of a medical device or implant can even be lower. Preferred amounts of testosterone or a derivative locally applied in accordance with the present invention in such coating are between 10 ng and 2.5 μg per $cm^2$ of the coated surface.

If another androgen receptor agonist or a testosterone derivative as defined herein is used instead of testosterone, the amount thereof locally applied is preferably equivalent with the above mentioned amounts of testosterone. For instance, androsterone is a testosterone analogue that has a potency that is approximately ⅐ of the potency of testosterone. Hence, if androsterone is used in accordance with the invention the amount applied is preferably 7 times the amount indicated above for testosterone.

The term "bisphosphonate" is well known in the art and refers to a class of drugs known for their inhibitory effect on osteoclastic bone resorption that have two phosphonate ($PO_3$) groups. A preferred bisphosphonate used in accordance with the present invention is selected from the group consisting of alendronate, risedronate, ibandronate, pamidronate, clodronate, zoledronate, etidronate, tiludronate, minodronate, olpadronate, neridronate, incadronate, and mixtures thereof. A more preferred bisphosphonate is selected from the group consisting of nitrogen containing bisphosphonates, preferably from the group consisting of alendronate, risedronate, ibandronate, pamidronate, zoledronate, minodronate, olpadronate, neridronate, incadronate. A particularly preferred bisphosphonate and salt are alendronate or alendronate sodium. The phrase "pharmaceutically acceptable salt" as used herein refers to the salts of a bisphosphonate that are suitable for use in the treatment of mammals, preferably humans, essentially without adverse effects, such as toxicity and allergic responses. The amount of the bisphosphonate or salt thereof, preferably alendronate or alendronate sodium, that is locally applied to the site of a bone fracture in accordance with the present invention is preferably such that no systemic effects of the bisphosphonate occur and, consequently, adverse effects of bisphosphonates such as suppression of bone turnover at a location other than the site of fracture, hypocalcemia and upper GI adverse effects are avoided. A preferred amounts of a bisphosphonate or salt thereof locally applied in accordance with the present invention is between 0.1 μg and 1 mg, more preferably between 0.1 μg and 500 μg more preferably between 1 μg and 250 μg, more preferably between 1.5 μg and 150 μg, more preferably between 2 and 100 μg, most preferably about 50 μg. This amount is preferably present in a patch or injectable depot forming formulation according to the invention. The amount of a bisphosphonate or salt thereof that is locally applied to the site of a bone fracture or defect as a coating of a medical device or bone implant can even be lower. Preferred amounts of a bisphosphonate or salt thereof locally applied in accordance with the present invention in such coating are between 20-500 ng and 2.5 μg per cm$^2$ of the coated surface. These amounts are preferably used if the bisphosphonate or salt thereof is alendronate or alendronate sodium. If zoledronate or a salt thereof is used in accordance with the invention the amount applied is preferably 20-80 times less than the amount indicated above because zoledronate is approximately 20-80 times more active as compared to alendronate. Hence, if zoledronate is locally applied in accordance with the present invention in a patch or injectable depot forming formulation the amount thereof is preferably between 1 ng and 50 μg, more preferably between 1 ng and 25 μg more preferably between 12.5 ng and 12.5 μg, more preferably between 20 ng and 7.5 μg, more preferably between 25 ng and 5 μg. Preferred amounts of zoledronate or a salt thereof locally applied in accordance with the present invention in a coating are between 0.25-25 ng per cm$^2$ of the coated surface.

Compositions according to the invention comprising at least one biodegradable polymer, an androgen receptor agonist and a bisphosphonate or pharmaceutically acceptable salt thereof can be either in solid form or in liquid or semi-solid form. The compositions are preferably for the local application to bone, in particular a bone fracture or bone defect.

In a preferred embodiment, compositions according to the invention are in solid form at room temperature and in vivo, i.e. at approximately 37° C. In that case, an implant comprising a composition of the invention or consisting of a composition of the invention can be implanted into a patient's body, for instance in the form of a patch. Provided is therefore also a patch comprising a composition according to the invention. A "patch" as used herein refers to a piece of solid, preferably flexible, material, such as a sheet comprising a biodegradable polymer and combination of active compound according to the invention. A patch according to the invention is particularly suitable for stimulating healing of compound and/or complicated fractures where the site of the fracture is accessible without the need for invasive methods and/or where the site of the fracture need to be accessed, for instance by an orthopedic surgeon, for supplementary treatment of the fractured bone or surrounding tissue or vasculature. A patch according to the invention is preferably applied to the facture site, more preferably the fracture site is covered with the patch. Alternatively, a patch according to the invention is preferably applied to the site of a bone defect, more preferably the site of the defect is covered with the patch. This way, the gradual release of the active compounds will be concentrated on the site of the fracture. The patch is thus preferably for the local application to bone, in particular a bone fracture or bone defect.

In order to aid in fracture healing a patch only need to release the active components to the fractured bone, i.e. the release of the active compounds only needs to be in one direction, which is toward the site of the fracture. Similarly, in order to stimulate adherence of a bone filer or implant to existing bone, a patch only need to release the active components to the site of a bone defect, i.e. the release of the active compounds only needs to be in one direction, which is toward the site of the defect. Provided are therefor also patches comprising a composition according to the invention which comprises a first layer comprising said composition according to the invention and a biodegradable second layer which is essentially impermeable for said androgen receptor agonist and said bisphosphonate or pharmaceutically acceptable salt thereof. Said second layer preferably also comprises or consists of at least one biodegradable polymer, which can be the same biodegradable polymer as present in the composition according to the invention, i.e. in the first layer of the patch, or a different biodegradable polymer. When applied to a fractured bone or bone defect, the first layer is the inner layer of the patch, facing the fractured bone of defect, and the second layer is the outer layer of the patch facing away from the fractured bone or defect. The presence of such layer prevents or at least reduced the amount of the active compounds that is released into the patient's body other than at the site of the bone fracture or defect. This may reduce unwanted effects of the active compounds and reduce the amount of active compounds that need to be present in the patch. As used herein "essentially impermeable" means that the amount of active compound is released from the second layer of the patch into or through the first layer of the patch over time is at most ⅕, preferably at most 1/10, more preferably at most 1/100, of the amount of drug that is released from the second layer of the patch into the direction of the fractured or defected bone.

A patch according to the invention may be prepared by e.g. dispersing or dissolving both active compounds, an androgen receptor agonist, preferably an anabolic steroid, more preferably testosterone or a derivative thereof, more preferably testosterone, and a bisphosphonate or pharmaceutically acceptable salt thereof, preferably alendronate, in a solution comprising at least one biodegradable polymer. After solidifying and optionally further processing of the composition this results in a patch wherein both active compounds are more or less evenly distributed in the patch, or in the first layer of the patch. Alternatively, two separate compositions can be prepared wherein each active compound is separately dispersed or dissolved in a solution comprising at least one, the same or different, biodegradable polymer. Each composition is subsequently solidified and optionally further processed separately, after which a patch is formed by combining the two solid formulations, a first formulation comprising at least one biodegradable polymer and an androgen receptor agonist and a second formulation comprising at least one biodegradable polymer and a bisphosphonate or pharmaceutically acceptable salt thereof. Combination of both solid formulations results in a single composition or patch comprising two parts, one comprising the androgen receptor agonist and the second comprising the bisphosphonate or salt thereof.

Further provided are injectable formulations comprising a composition according to the invention. Such injectable formulations are liquid, gelled or semi-solid at storage temperature (typically 2-8° C.) and/or at room temperature (typically 15-25° C.) but solidify in situ, i.e. at a temperature of approximately 37° C. As used herein the term "injectable formulation" refers to a formulation that can be applied to a fractured bone by injection and that is intended to solidify and consequently remains at the site of injection. Such injectable formulation can also be applied to a site of a bone defect. As used herein, "solidify in situ" refers to an increase in viscosity of an injectable formulation after administration to a patient sufficient to allow the formulation to remain at the site of injection, e.g. to a solid semi-solid, paste-like or gel-like form. The injectable formulations of the invention have a viscosity suitable for injection, e.g. injectable using a syringe, when at room temperature. The viscosity of the injectable in situ depot formulation is preferably between 300 and 800 mPas. Such injectable formulation is for instance in the form of a liquid or gel. After solidifying at the location of the injection, which is the site of the bone fracture or bone defect, the formulation functions as a depot formulation gradually releasing at least the androgen receptor agonist, preferably testosterone or the derivative thereof, more preferably testosterone, nandrolone or dihydrotestosterone, over time. Because bisphosphonates accumulate in bone after release and thus may exert their activity for a prolonged period of time even if it is released within a short period of time, bisphosphonates do not need to be released gradually from the depot formulation or patch. Preferably the depot formulation gradually release both of the active compounds, i.e. the androgen receptor agonist and the bisphosphonate or pharmaceutically acceptable salt thereof. Hence, an injectable formulation according to the invention is preferably an injectable in situ depot forming formulation. The injectable formulation is thus preferably for the local application to bone, in particular a bone fracture or bone defect.

An injectable in situ depot formulation according to the invention is for instance applied by administering the formulation across the site of a bone fracture, so that the resulting depot formulation after solidifying covers a substantial portion, i.e. at least 25%, preferably at least 50%, more preferably at least 75%, of the site of fracture. Most preferably essentially the entire site of the fracture is covered by the solidified depot formulation. The injectable in situ depot forming formulation can be applied to the site of fracture in a single injection or by multiple injections.

Further provided are bone fillers comprising a composition according to the invention. The term "bone filler" as used herein is well known in the art and is also referred to as "bone void filler". The term refers to a material that can be used to fill gaps or voids in bone. The most common type of bone fillers are bone cement and demineralized bone matrix. Demineralized bone matrix (DBM) is allograft bone from donated human tissue from which the inorganic minerals have been removed, as well as most of the cells, so that a collagen matrix remains. The demineralized bone is then combined with a biocompatible carrier to provide the demineralized bone matrix. Suitable materials for use as biocompatible carriers are hyaluronic acid, dextran and pluronic block copolymers of polyethylene oxide and polypropylene. "Bone cement" is well known in the art and refers to a material that can be administered in or around bone, e.g. to fill gaps or voids, or between a bone implant and the surrounding bone to secure an implant or a screw or a plate to the existing bone. The most commen types of bone cement are cements comprising polymethylmethacrylate (PMMA) or PMMA and MMA copolymer blends and calcium phosphate cement, e.g. comprising tetracalcium phosphate, tricalcium phosphate and/or dicalcium phosphate anhydrous, or composites thereof. Bone cements are generally provided as two-component materials. The two components of PMMA/MMA based cements are mixed upon which polymerization is induced resulting in a change in viscosity of the cement so that it can be locally applied, after which it hardens into solid cement at the site of application. A calcium phosphate cement typically consists of a powder and a liquid phase. When mixed with water the powder composition forms hydroxyapatite.

A composition according to the invention comprising a biodegradable polymer, an androgen receptor agonist, preferably testosterone or derivative thereof, and a bisphosphonate, is for instance mixed with one or more of the bone cement components or before these are mixed and hardened or with the demineralized bone matrix. The composition of the invention is for instance mixed with the one or more bone cement components or with the components making up the demineralized bone matrix in the form of microspheres before being applied at the site of a bone defect or fracture and thus before the filler is hardened. Provided is therefore a bone filler comprising a composition according to the invention. Preferably said composition is present in the form of microspheres in the bone filler. Provided is therefore a bone filler comprising microspheres comprising a composition according to the invention The microsphere for instance have an average size of 1 µm to 1000 µm. The bone filler is preferably a bone cement or a demineralized bone matrix.

Alternatively, a composition according to the invention can be applied to the surface of a bone filler in the form of a coating. Such coating comprising a composition according to the invention is also suitable for use with medical devices and bone implants. The coating is thus preferably for the local application at the site of bone, in particular a bone fracture or bone defect. Further provided is therefore a coating, preferably for bone fillers, bone implants and/or medical devices, comprising a composition comprising at least one biodegradable polymer, an androgen receptor agonist and a bisphosphonate or pharmaceutically acceptable salt thereof according to the invention. Also provided is a bone filler, medical device or bone implant provided with a coating according to the invention. A coating according to the invention may be prepared by e.g. dispersing or dissolving both active compounds, an androgen receptor agonist, preferably an anabolic steroid, more preferably testosterone or a derivative thereof, more preferably testosterone, and a bisphosphonate or pharmaceutically acceptable salt thereof, preferably alendronate, in a solution comprising at least one biodegradable polymer. The coating can be applied to the appropriate item and thereafter solidified, e.g. by cooling. The term "coating", as used herein, includes coatings that completely cover a surface of a bone filler, medical device or bone implant, or a portion thereof. A coating preferably covers at least 50% of the surface of a bone filler, medical device or bone implant. The term "medical device" as used herein refers to any type of device that can be used in the human or animal body, preferably in or around bone tissue, and includes, but is not limited to, screws, bone plates, pins and spinal rods. Such medical device is preferably a medical device for use in bone tissue. The term "bone implant" as used herein refers to any type of implant that can be introduced in or attached to bone and includes, but is not limited to, dental implants, spinal implants and replacement joints, including, but not limited to knee, hip, ankle, shoulder, elbow, and wrist joints.

As indicated herein before, the combined treatment with an androgen receptor agonist, preferably testosterone or a derivative thereof, and a bisphosphonate or pharmaceutically acceptable salt thereof is at least in part the result of a synergistic effect of the two active compounds, in particular of the anabolic effect of the androgen receptor agonist and the anti-catabolic effect of the bisphosphonate when administered locally at the site of a bone fracture or defect. When used as a coating of medical devices or bone implants and in or on the surface of bone fillers, the combination of an androgen receptor agonist, preferably testosterone or a derivative thereof, and a bisphosphonate or pharmaceutically acceptable salt thereof is thought to stimulate the formation of new bone, in particular in the early stages after the bone filler and/or implant has been introduced of at the site of a bone fracture or defect. As a result thereof, the attachment of the bone filler, medical device such as a screw, plate or pin, and bone filler and/or implant to the existing bone is improved and occurs more rapidly, and the healing of a fracture, if present, is stimulated.

Patches or injectable depot forming formulations according to the invention as described above are also suitable for stimulating formation of new bone in bone defects where a bone void filler and/or bone implant has been introduced into the site of the bone defect. The patch or injectable depot forming formulation is applied to the site of a bone defect in a manner as explained above in such a way that it covers the interface between bone and bone filler and/or bone implant. The combined activity of an androgen receptor agonist, preferably testosterone or a derivative thereof, and a bisphosphonate or pharmaceutically acceptable salt thereof in such path or injectable depot formulation stimulate the attachment of the bone filler and/or bone implant to the existing bone.

Patches, depot formulations, bone fillers and coatings according to the invention gradually release at least one of the two active compounds when administered locally at the site of a bone fracture. Preferably at least the androgen receptor agonist, preferably testosterone or derivative thereof, is gradually released from the depot formulation, patch, bone filler or coating. Because bisphosphonates accumulate in bone after release and thus may exert their activity for a prolonged period of time even if it is released within a short period of time, bisphosphonates do not need to be released gradually from the depot formulation, patch, bone filler or coating. Preferably the depot formulation, patch, bone filler or coating gradually releases both of the active compounds, i.e. the androgen receptor agonist and the bisphosphonate or pharmaceutically acceptable salt thereof. As used herein "gradually" preferably means that the androgen receptor agonist, preferably testosterone or derivative thereof, or both of the active compounds are released from the depot formulation, patch, bone filler or coating over a period of time of between 1 day and 4 months after administration or application to the site of fracture or defect. Preferably the androgen receptor agonist or both of the active compounds are released from the depot formulation, patch, bone filler or coating over a period of time of between 1 day and 12 weeks, more preferably of between 1 day and 10 weeks, most preferably of between 2 and 10 weeks, such as e.g. approximately 4, 5, 6, 7 or 8 weeks. In a solid composition or patch according to the invention comprising two separate parts, each comprising one of the active compounds, it is possible to select the biodegradable polymers in each part such that the release characteristics of the an androgen receptor agonist and the bisphosphonate or salt thereof are not the same. For instance, it is possible to select the type, molecular weight and amount of polymer(s) such that the bisphosphonate or salt is released over a shorter period of time as compared to the androgen receptor agonist.

Compositions, injectable formulations, patches, bone fillers and coatings according to the invention further comprise at least one biodegradable polymer. Preferably, the compositions, injectable formulations, patches and coatings are biodegradable in their entirety. Provided are therefor biodegradable compositions, injectable formulations, patches and coatings according to the invention. The term "biodegradable" as used herein refers to a material that gradually dissolves, decomposes, hydrolyzes and/or erodes in vivo. Generally, the "biodegradable polymers" herein are polymers that are hydrolysable, and/or in vivo through hydrolysis and/or enzymatic action. The term "biodegradable polymer" as used herein includes any biodegradable synthetic polymers and natural polymers that can be used and are degradable in vivo. The advantage of the use of biodegradable polymers is that the compositions, injectable formulation, patches and coatings according to the invention do not need to be removed from the patient's body after the active compounds have been released.

Any biodegradable polymer or copolymer known in the art that can be used to gradually release active compounds in vivo can be used in the compositions, injectable formulations and patches of the invention. Suitable biodegradable polymers and copolymers and methods for their are for instance described in WO 2011/161531, WO 2010/018159, WO 2005/068533, WO 2013/015685, WO 2012/175746 and WO 2012/175748, which are incorporated herein by reference. Examples of suitable biodegradable polymers and copolymers include, but are not limited to, polylactides, polyglycolides, polycaprolactones, polydioxannones, polycarbonates, polyhydroxybutyrates, polyalkyene oxalates, polyanhydrides, polyamides, polyurethanes, polyesteramides, polyacetals, polyketals, polyorthocarbonates, polyphosphazenes, polyhydroxyvalerates, polyalkylene succinates, polymalic acid, polyorthoesters, and copolymers, block copolymers, and mixtures thereof, such as poly-D, L-Lactide (PDLLA), copolymers of lactide and glycolide (PLGA), copolymers of lactide and ε-caprolactone, poly (lactide-ε-caprolactone) (PLA-ε-CL) copolyesters and polylactide-trimethylenecarbonate copolymer and amino acid-based polymers such as tyrosine-based polyarylates and polycarbonates, and leucine and/or lysine-based polyester urethanes and polyester-amides. Preferred biodegradable polymers are polylactides, polyglycolides, poly (glycolide-ε-caprolactone), poly (glycolide-D, L-Lactide), poly (DL-Lactide), poly (glycolide-ε-caprolactone), amino acid-based polyester urethanes and amino acid-based polyester-amides.

The selection of kind of biodegradable polymer, the type of polymer (a single monomer or a co-polymer), the molecular weight of the biodegradable polymer, and amount of biodegradable polymer for the compositions, formulations, patches, bone fillers and coatings of the invention generally depend upon the desired properties of the patches, depot formulations, bone fillers and coatings. For example, the type, molecular weight, and amount of biodegradable polymer can influence the period of time during which the active compounds are released from the patches, depot formulations, bone fillers and coatings., as indicated herein above. In addition to the period of time during which the active compound are released, the kinetics of release can be influence by the choice of kind, type, amount, molecular weight, etc. of the polymer or combination of polymers. For instance, the polymer(s) can be selected such that an initial burst release of one or both of the active compounds occurs after applying the injectable in situ patches, depot formulations, bone fillers and coatings according to the invention to the site of fracture or defect. In that case for instance, 1%, In a preferred embodiment, the at least one biodegradable polymer is an amino acid based or amino acid containing polymer. Particularly preferred are amino acid based biodegradable polyester urethanes and amino acid based biodegradable polyester amides. Such polymers for instance have the advantage that they can be chosen such that they predominantly degraded in vivo by enzymatic activity as a result of which release of the active compounds mainly follows zero-order kinetics. Particularly preferred amino acid based polymers are described in WO 2012/175746 and WO 2012/175748. Described herein are amino acid based polyester amides (PEA) of formula

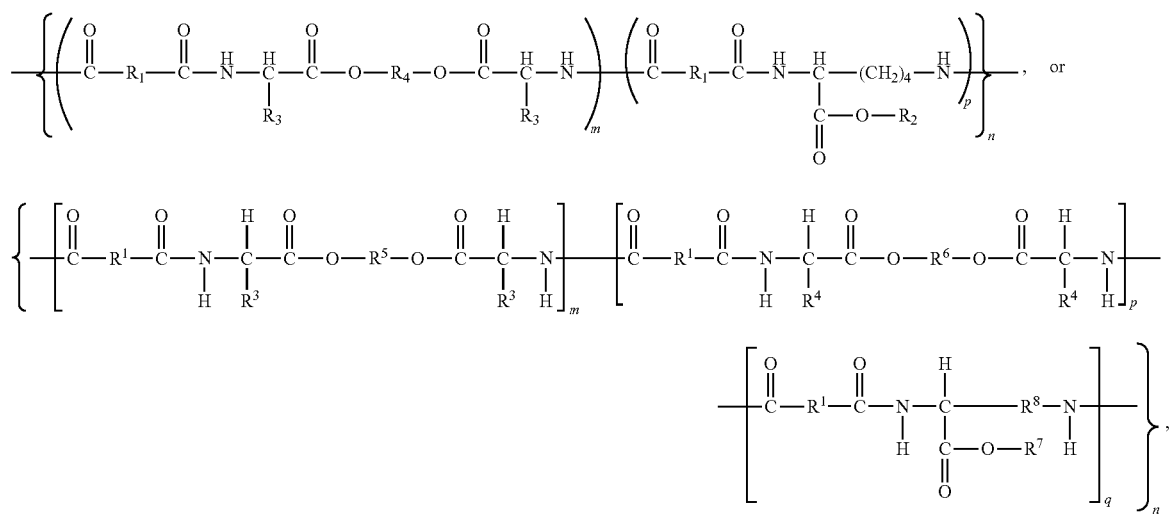

5%, 10% or even higher of one of the active compounds or both active compounds is released within e.g. 4 or 8 hours of application to the fracture site. However, it is preferred that such initial burst release is prevented and that the release of both active compounds occurs via zero order kinetics, meaning that the release of the active compounds from the patch, depot formulation, bone filler and coating is essentially linear over time. Hence, in a preferred embodiment, a depot formulation, patch, bone filler or coating displays zero order release kinetics for both the androgen receptor agonist, preferably testosterone or a derivative thereof, more preferably androgen receptor agonist, and for the bisphosphonate or pharmaceutically acceptable salt thereof, preferably alendronate or alendronate sodium.

Furthermore, the desired viscosity also determines the type, kind, and amount of biodegradable polymer that is used in the compositions, injectable formulations, patches, bone fillers and coatings of the invention. For instance, if a composition according to the invention is used to produce an injectable in situ depot forming formulation, a biodegradable polymer or combination of polymers is preferably selected that has a viscosity at room temperature that is suitable for injection and that solidifies at a temperature of approximately 37° C. Alternatively, if a composition according to the invention is used to prepare a patch or coating, a biodegradable polymer or combination of polymers is preferably selected that has a viscosity suitable to dissolve or disperse the active compounds at elevated temperature, e.g. above 42° C., preferably above 50° C., and that is solid at room temperature and at a temperature of approximately 37° C.

wherein:

m varies from 0.1 to 0.9; p varies from 0.9 to 0.1; n varies from 50 to150;

each R1 is independently (C1-C20)alkylene;

each R2 is independently hydrogen or (C6-C10)aryl(C1-C6)alkyl;

each R3 is independently hydrogen, (C1-C6) alkyl, (C2-C6)alkenyl, (C2-C6)alkynyl, or (C6-C10)aryl(C1-C6)alkyl; and each R4 is independently (C2-C20)alkylene.

Preferably m varies from 0.01 to 0.99; p varies from 0.2 to 3 and q varies from 0.10 to 1.00 whereby n is 5 to 100; R1 is —(CH2)8; R3 and R4 in the backbone units m and p is leucine, —R5 is hexane, and R6 is a bicyclic-fragments of 1,4:3,6-dianhydrohexitols of structural formula

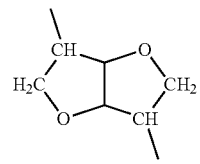

R7 is chosen from H or a benzyl group and R8 is —(CH2)4—.

Particularly preferred amino acid based PEA copolymers described in WO 2012/175746 and WO 2012/175748 have the formula

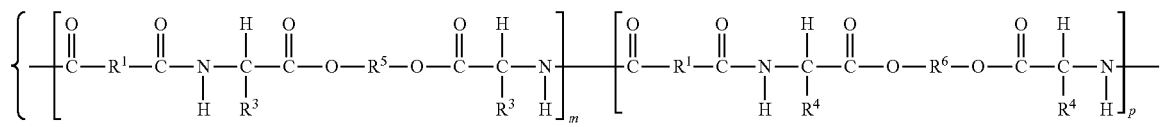

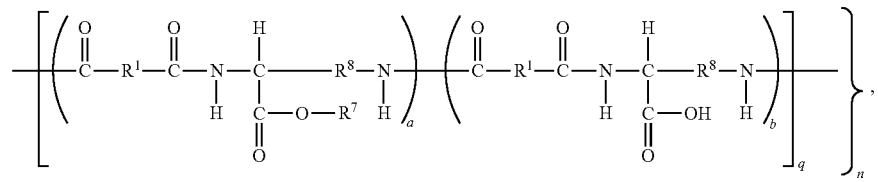

wherein
m+p varies from 0.9-0.1 and q varies from 0.1 to 0.9;
m+p+q=1 whereby m or p can be 0;
n varies from 5 to 300;
R1 is independently selected from the group consisting of (C2-C20) alkylene, (C2-C20) alkenylene, —(R9—CO—O—R10—O—CO—R9)—, —CHR11—O—CO—R12—COOCR11— and combinations thereof;
R3 and R4 in a single backbone unit m or p, respectively, are independently selected from the group consisting of hydrogen, (C1-C6)alkyl, (C2-C6)alkenyl, (C2-C6)alkynyl, (C6-C10)aryl, (C1-C6)alkyl, —(CH$_2$)SH, —(CH$_2$)$_2$S(CH$_3$), —CH$_2$OH, —CH(OH)CH$_3$, —(CH$_2$)$_4$NH$_3$+, —(CH$_2$)$_3$NHC(=NH$_2$+)NH$_2$, —CH$_2$COOH, —(CH$_2$)COOH, —CH$_2$—CO—NH$_2$, —CH$_2$CH$_2$—CO—NH$_2$, —CH$_2$CH$_2$COOH, CH$_3$—CH$_2$—CH(CH$_3$)—, (CH$_3$)$_2$—CH—CH$_2$—, H$_2$N—(CH$_2$)$_4$—, Ph-CH$_2$—, CH=C—CH$_2$—, HO-p-Ph-CH$_2$—, (CH$_3$)$_2$—CH—, Ph-NH—,

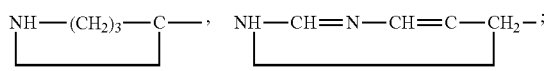

R5 is selected from the group consisting of (C2-C20) alkylene, (C2-C20)alkenylene, alkyloxy or oligoethyleneglycol;
R6 is selected from bicyclic-fragments of 1,4:3,6-dianhydrohexitols of formula

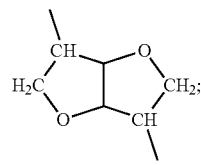

R7 is selected from the group consisting of (C6-C10)aryl (C1-C6)alkyl;
R8 is —(CH$_2$)$_4$—;
R9 or R10 are independently selected from C2-C12 alkylene or C2-C12 alkenylene;
R11 or R12 are independently selected from H, methyl, C2-C12 alkylene or C2-C12 alkenylene and whereby a is at least 0.05, b is at least 0.05 and a+b=1.

Such amino acid based PEAs can be prepared using methods known in the art, for instance as described in scheme 1 of WO 2012/175746 and WO 2012/175748. It is described that the polyesteramides are synthesized by solution polycondensation of para-toluene sulfonate di-amine salts with activated di-acids. Typically dimethylsulfoxide or dimethylformamide are used as solvent and triethylamide is used as a base and the reaction is typically carried out under an inert atmosphere at 60° C. for 24-72 hours under constant stirring. The reaction mixture is then purified via water precipitation, followed by an organic precipitation and filtration, followed by drying under reduced pressure to yield the polyesteramide.

In another preferred embodiment, the at least one biodegradable polymer is a multi-block co-copolymer comprising at least two hydrolysable segments derived from two different pre-polymers. Particularly preferred are multi-block co-polyester comprising of a glycolide-ε-caprolactone segment and a lactide-glycolide segment. Such co-polymers for instance have the advantage that they can be chosen such that they predominantly degraded in vivo via surface erosion as a result of which release of the active compounds mainly follows zero-order kinetics. Particularly preferred multi-block co-copolymer are described in WO 2005/068533 and WO 2013/015685.

WO 2005/068533 describes multi-block copolymer, comprising at least two hydrolysable segments derived from pre-polymers A and B, which segments are linked by a multi-functional chain-extender and are chosen from the pre-polymers A and B, and triblock copolymers ABA and BAB, wherein the multi-block copolymer is amorphous at physiological (body) conditions. Said chain extender is preferably derived from a difunctional aliphatic compound, preferably a diisocyanate, such as 1,4-butanediisocyanate. Said pre-polymer (A) preferably comprises reaction products of at least one cyclic monomer with at least one non-cyclic initiator selected from the group of diols, dicarboxylic acids and hydroxycarboxylic acids, wherein said cyclic monomer is preferably selected from the group of glycolide, lactide (L, D or DL), ε-caprolactone, δ-valerolactone, trimethylene carbonate, tetramethylenecarbonate, 1,4-dioxane- 2-one (para-dioxanone), 1,5-dioxepane-2-one and/or cyclic anhydrides such as oxepane-2, 7-dione. Said pre-polymer (B) preferably comprises ε-caprolactone, δ-valerolactone, trimethylene carbonate, para- dioxanone, DL-lactide and/or glycolide, more preferably said pre-polymer (B) contains d, l-lactide, and is preferably poly (d, l-lactide) or poly (lactide-glycolide (50/50)), wherein pre-polymer (B) preferably has a number average molecular weight (Mn) higher than 300.

WO 2013/015685 describes semi-crystalline, phase separated, thermoplastic multi-block copolymer, the copolymer being characterized in that:

a) it comprises at least one hydrolysable pre-polymer (A) segment and at least one hydrolysable pre-polymer (B) segment, b) said multi-block copolymer having a glass transition temperature (Tg) of 37° C. or less and a melting point (Tm) of 110-250° C. under physiological conditions;

c) the segments are linked by a multifunctional chain-extender;

d) the segments are randomly distributed over the polymer chain;

e) at least part of the pre-polymer (A) segment is derived from a water-soluble polymer. Said chain-extender is preferably a difunctional aliphatic chain-extender, preferably a diisocyanate, such as 1,4-butane diisocyanate. Said pre-polymer (A) preferably comprises reaction products of cyclic monomers and/or non cyclic monomers, wherein said non cyclic monomers are preferably selected from the group consisting of succinic acid, glutaric acid, adipic acid, sebacic acid, lactic acid, glycolic acid, hydroxybutyric acid, ethylene glycol, diethylene glycol, 1,4-butanediol and/or 1,6-hexanediol, and wherein said cyclic monomers are preferably selected from the group consisting of glycolide, lactide, ε-caprolactone, δ-valerolactone, trimethylene carbonate, tetramethylenecarbonate, 1,5-dioxepane-2-one, 1,4-dioxane-2-one (para-dioxanone) and/or cyclic anhydrides such as oxepane-2,7-dione. Said pre-polymer (B) segment preferably comprises a crystallisable polymer derived from hydroxyalkanoate, glycolide, L-lactide or D-lactide, preferably L-lactide pre-polymers and D-lactide pre-polymers in such amounts and ratio that stereocomplexation between L-lactide and D-lactide is achieved, more preferably said pre-polymer (B) is poly(L-lactic acid) with an Mn of 1000 g/mol or more.

Such co-polymers are particularly preferred for use in the compositions of the present invention. Such multi-block co-polymers can be prepared using methods known in the art, for instance by chain-extending a mixture of the pre-polymers, containing the monomers, in the desired ratio with an equivalent amount of a di-functional molecule, preferably an aliphatic molecule, such as a diisocyanate such as 1,4-butanediisocyanate as described in WO 2005/068533 and WO 2013/015685.

The two active compounds an androgen receptor agonist and a bisphosphonate or pharmaceutically acceptable salt thereof are for instance dissolved or dispersed in a solution of the at least one biodegradable polymer at a temperature where the polymer is liquid, conveniently e.g. room temperature or at elevated temperature in case the composition is solid at room temperature. A sterile product can be obtained by aseptic production or sterilization following production.

Optionally the compositions according the invention contain one or more excipients. The excipient or excipients may be added to a solution of the at least one biodegradable polymer. For instance, excipients may be present that modify the physical and/or mechanical properties of the biodegradable polymer(s), such as improving the solubility of the polymer and/or the active compounds, improving the dispersion of the active compounds in a solution of the polymer(s) or modulating the release of the active compounds from the depot formulation, patch, bone filler or coating according to the invention. In addition, excipients that function as a solvent for the biodegradable polymer may be included in the compositions of the invention. Examples of suitable excipients are well known in the art and include, but are not limited to solvents, surfactants, dispersing agents and thickening agents, more in particular methanol, ethanol, propylene glycol, Tweens, poly(ethylene glycol), polyvinyl alcohol, lactic acid, acetic acid, alginic acid, carboxymethylcellulose, gelatin, chitosan, guar gum, hydroxyethylcellulose, hydroxyethylmethyl cellulose, starch, pregelatized starch, hydroxypropylstarch, methyl cellulose, pectin, glycerol, N, N dimethylacetamide, benzyl benzoate, polyoxyethylated fatty acid, lecithin, soybean oil, vegetable oils and cotton seed oils. The concentration of the excipients is typically from 1% to 50% by weight of the composition, preferably from 1% to 30% by weight of the compositions, more preferably from 1% to 20% by weight of the composition.

The compositions, injectable in situ depot forming formulations, patches, bone fillers and coatings of the invention are suitable for treatment of bone fractures and/or bone defects. In particular, the compositions, formulations, patches, bone fillers and coatings are suitable for accelerating fracture healing. The compositions, formulations, patches, bone fillers and coatings are further particularly suitable for accelerating attachment of a bone filler and/or implant to existing bone. Provided is therefore a composition comprising an androgen receptor agonist, preferably an anabolic steroid, more preferably testosterone or a derivative thereof, more preferably testosterone, nandrolone or dihydrotestosterone and a bisphosphonate or pharmaceutically acceptable salt thereof, preferably alendronate or alendronate sodium, for use in a method of treatment of a bone fracture or a bone defect. Also provided is a composition comprising an androgen receptor agonist, preferably an anabolic steroid, more preferably testosterone or a derivative thereof, more preferably testosterone, nandrolone or dihydrotestosterone, and a bisphosphonate or pharmaceutically acceptable salt thereof, preferably alendronate or alendronate sodium, for use in a method of bone fracture healing. Said methods preferably comprise applying a composition according to the invention comprising at least one biodegradable polymer, an androgen receptor agonist and a bisphosphonate or pharmaceutically acceptable salt thereof to a site of fracture or defect, more preferably applying an injectable in situ forming depot formulation or a patch according to the invention to a site of fracture or defect. Alternatively said methods comprise introducing a bone filler comprising a composition according to the invention or a bone filler, a medical device or implant provided with a coating according to the invention to or into a site of bone fracture or bone defect. In yet another embodiment, said methods comprise a combination thereof and thus comprise introducing a bone filler comprising a composition according to the invention or a bone filler, a medical device or implant provided with a coating according to the invention to or into a site of bone fracture or bone defect and applying an injectable in situ forming depot formulation or a patch according to the invention to a site of fracture or defect. Said depot formulation, patch, bone filler or coating most preferably comprises testosterone and alendronate or a salt thereof.

Also provided is the use of an androgen receptor agonist, preferably an anabolic steroid, more preferably testosterone or a derivative thereof, more preferably testosterone, nandrolone or dihydrotestosterone, and a bisphosphonate or pharmaceutically acceptable salt thereof, preferably alendronate or alendronate sodium, for the preparation of a medicament for the treatment of a bone fracture or a bone defect. Said treatment preferably comprises applying a composition according to the invention comprising at least one biodegradable polymer, an androgen receptor agonist and a bisphosphonate or pharmaceutically acceptable salt thereof to a site of fracture or defect, more preferably applying an injectable in situ forming depot formulation or a patch according to the invention to a site of fracture or defect. Alternatively said methods comprise introducing a bone filler comprising a composition according to the invention or a bone filler, a medical device or implant provided with a coating according to the invention to or into a site of bone fracture or bone defect. In yet another embodiment, said methods comprise a combination thereof, and thus comprise introducing a bone filler comprising a composition according to the invention or a bone filler, a medical device or implant provided with a coating according to the invention to or into a site of bone fracture or bone defect and applying an injectable in situ forming depot formulation or a patch according to the invention to a site of fracture or defect. Said depot formulation, patch, bone filler or coating most preferably comprises testosterone and alendronate or a salt thereof.

The invention further provides a method of treating a bone fracture or defect in a patient, preferably a human patient or other mammal, comprising administering to a site of fracture or defect a patch or injectable in situ depot forming formulation according to the invention. Further provided is a method of bone fracture healing comprising administering to a site of fracture a patch or injectable in situ depot forming formulation according to the invention. Said patch or injectable in situ depot forming formulation preferably comprises a therapeutically effective amount of testosterone, nandrolone or dihydrotestosterone, more preferably testosterone, and alendronate or alendronate sodium, most preferably alendronate sodium. The invention further provides a method of treating a bone fracture or defect in a patient, preferably a human patient or other mammal, comprising introducing a bone filler comprising a composition according to the invention or a bone filler, a medical device or implant provided with a coating according to the invention to or into a site of bone fracture or bone defect. Also provided is a method of treating a bone fracture or defect in a patient, preferably a human patient or other mammal, comprising administering to a site of fracture a patch or an injectable in situ forming depot formulation according to the invention and introducing a bone filler comprising a composition according to the invention or a bone filler, a medical device or bone implant provided with a coating according to the invention to or into a site of bone fracture or bone defect. The term "patient" as used herein refers to human and any non-human subject that can suffer from a bone fracture or bone defect. Preferably, a patient as used herein is a mammal. Preferred examples of patients include, but are not limited to, humans, dogs and other canines, cats and other felines, horses, cows and other bovines, mice, rats, rabbits, guinea pigs and other rodents, monkeys and other primates, pigs and swine, and the like. A particularly preferred patient is a human patient.

Further provided is a method of bone fracture healing comprising administering to a site of fracture a patch or injectable in situ depot forming formulation according to the invention. Said patch, injectable in situ depot forming formulation, bone filler or coating preferably comprises a therapeutically effective amount of testosterone, nandrolone or dihydrotestosterone, more preferably testosterone, and alendronate or alendronate sodium, most preferably alendronate sodium.

The term "bone fracture" as used herein includes traumatic fracture and pathological fractures, both simple and compound fractures. The uses and methods of the invention are particularly suitable for treatment of complicated bone fractures, preferably traumatic complicated bone fractures. As used herein, the term "complicated fracture" refers to a fractures that is accompanied by injury to surrounding tissue, such as nerves and blood vessels, and/or surrounding organs. A complicated fracture is often, but not necessarily, a compound or open fracture. The uses and methods of the invention are further particularly suitable for treatment of pathological bone fractures. A preferred fracture that is treated in accordance with the invention is a fracture that requires treatment by an orthopedic surgeon. an orthopedic surgeon for instance stabilizes the fracture, for instance using screws. Such fractures are in particular advantageously treated by applying a patch according to the invention. Examples of fractures that are advantageously treated in accordance with the invention are fractures of the spine, leg and arm. A further example of a fracture that is advantageously treated in accordance with the present invention is a vertebral compression fracture. Such fracture occurs when one or more of the bones of the vertebral column fractures or collapses, typically when the vertebrae are already weakened for instance as a result of ageing or a disease that weakens bone, such as osteoporosis, Paget's disease or bone cancer. Yet another example are complete fractures that are characterized by the fact that a gap is present between bone part or fragments. Usually spontaneous healing of such fractures occurs very slow. Therefore, such fractures in particular benefit from the treatments provided by the present invention. Provided is therefore a method or use according to the invention wherein said fracture is a complicated fracture, preferably a traumatic complicated fracture, or a pathological fracture. A patient treated in accordance with the invention is preferably a patient suffering from a complicated fracture, preferably a traumatic complicated fracture, or a pathological fracture. A further preferred fracture treated with a patch or injectable in situ depot forming formulation is a vertebral compression fracture.

Features may be described herein as part of the same or separate aspects or embodiments of the present invention for the purpose of clarity and a concise description. It will be appreciated by the skilled person that the scope of the invention may include embodiments having combinations of all or some of the features described herein as part of the same or separate embodiments.

The invention is further explained in the following Example. This Example does not limit the scope of the invention, but merely serve to clarify the invention.

BRIEF DESCRIPTION OF THE DRAWING

FIGURE. Induction of activity of MC3T3 cells by alendronate, dihydroxytestosterone (Stanolone) and combinations thereof. ALP: alkaline phosphatase, AP: acidic phosphatase.

EXAMPLE

Materials and Methods
Cells and Treatment
MC3T3-E1 (ECACC, Acc. No. 99072810) were cultured in α-MEM (Invitrogen, Carlsbad, Calif.) supplemented with 100 U/ml penicillin, 100 ug/ml streptomycin (Invitrogen, Carlsbad, Calif.) and 5% fetal bovine serum (Hyclone, GE Healthcare). Cells were grown under standard conditions (37° C., 5% CO2 and 95% humidity). MC3T3-E1 cells were seeded at a density of 26000 cells/cm2 and seeding of the cells was considered as the day 0 timepoint. On day 1 post-plating, the medium of the MC3T3-E1 cells was replaced with osteogenic medium (the above-mentioned media supplemented with 50 μg/ml Ascorbic Acid (Sigma)), 10 nM β-glycerol phosphate (Sigma) and on day 3 post-plating, hormones or vehicle (0.1% ethanol) were added.

The compound tested were Stanolone (dihydroxytestosterone (DHT)) in combination with alendronate or alendronate only. The final Stanolone concentrations used were: 3 nM, 15 nM, 75 nM and 375 nM Stanolone (TCI Europe N.V.) in 0.1% ethanol and 2, 10, 50 μM Alendronate (TCI Europe N.V.) in milliQ. The final concentration ethanol for the cultures was 0.1%. The medium was changed every 2-3 days.

Alkaline Phosphatase and Acidic Phosphatase Activity Assay

Cells were lysed for 10 minutes with lysisbuffer (100 mM Potassium phosphate, 0.2% Triton X-100, pH 7.8 containing protease inhibitor cocktail (Roche)). To determine the alkaline phosphatase activity, CDP-star (Roche) was added to the lysates and incubated for 30 minutes in an 96-wells optiplate in the dark. The luminescence (1 second) was measured with a Filtermax F5 (Molecular Devices).

The acidic phosphatase activity of the cells was determined by adding freshly prepared p-NPP buffer (4-nitrophenyl phosphate (Sigma) in 0.1 M NaAc+0.1% Triton X-100, pH5.5) to the cell lysates and incubated for 1.5 hrs at 37° C. and 5% CO2. The reaction was stopped by adding 10 μNaOH. The absorbance was measured at 405 nm with a Filtermax F5 (Molecular Devices).

Statistical Analysis

All data are presented as mean±SEM. Data were analysed using Student's t-test at *p<0.05, or p<0.01 or *p<0.001 as compared to Alendronate only (0 nM Stanolone).

Results

To test whether alendronate and the combination of alendronate and DHT (Stanolone) are able to induce the activity of osteoblast cells, MC3T3 cells were stimulated in medium +/− compounds for a total of 10 days. The activity of osteoblast cells was than measured by analyzing the amount of ALP enzyme, a well-established marker for bone cell activity. The final data were than corrected for acidic phosphatase to correct for the total number of cells. The data obtained show that treatment of MC3T3 cells with alendronate only (0 nM Stanolone) results in a small increase of ALP/AP activity at concentrations of 2 and 10 μM whereas 50 μM decreases ALP/AP activity (FIGURE). In contrast, treatments with alendronate in combination with Stanolone (3, 15, 75 and 375 nM Stanolone) result in strong and significant increase of ALP activity as compared to alendronate only (FIGURE).

REFERENCES

Aspenberg P, Wermelin K, Tengwall P, Fahlgren A. Additive effects of PTH and bisphosphonates on the bone healing response to metaphyseal implants in rats. Acta Orthop. 2008 Feb.; 79(1):111-5.

Cheng B H, Chu T M, Chang C, Kang H Y, Huang K E. Testosterone delivered with a scaffold is as effective as bone morphologic protein-2 in promoting the repair of critical-size segmental defect of femoral bone in mice. PLoS One. 2013 Aug. 5; 8(8):e70234.

Einhorn, T A. Can an anti-fracture agent heal fractures? Clin Cases Miner Bone Metab. 2010 Jan.; 7(1):11-4.

Wermelin K, Aspenberg P, Linderbäck P, Tengvall P. Bisphosphonate coating on titanium screws increases mechanical fixation in rat tibia after two weeks. J Biomed Mater Res A. 2008 Jul.; 86(1):220-7.

Xue D, Li F, Chen G, Yan S, Pan Z. Do bisphosphonates affect bone healing? A meta-analysis of randomized controlled trials. J Orthop Surg Res. 2014 Jun. 5; 9:45.

The invention claimed is:

1. A method for local treatment of a bone fracture or bone defect in a patient, the method comprising:
    applying onto or into a site of bone fracture or bone defect a formulation comprising:
    at least one biodegradable polymer;
    a testosterone, dihydrotestosterone or an ester thereof; and
    an alendronate or pharmaceutically acceptable salt thereof;
    wherein the method stimulates formation of new bone at the site of the bone fracture or bone defect by inducing osteoblast activity.

2. The method of claim 1, wherein the amount of said alendronate or salt thereof in the formulation is between 0.1 μg and 1 mg and the amount of said testosterone, dihydrotestosterone or an ester thereof in the formulation is between 20 μg and 10 mg.

3. The method of claim 1, wherein the formulation is a coating.

4. The method of claim 3, wherein the coating is a coating for a medical device or bone implant.

5. The method of claim 1, wherein said formulation is contained in a bone filler or patch.

6. The method of claim 1, wherein the bone fracture or bone defect is covered by the formulation.

7. The method of claim 1, wherein the formulation is in the form of microspheres.

8. The method of claim 1, wherein the at least one biodegradable polymer is selected from the group consisting of polylactides, polyglycolides, polycaprolactones, polydioxannones, polycarbonates, polyhydroxybutyrates, polyalkyene oxalates, polyanhydrides, polyamides, polyesteramides, polyurethanes, polyacetals, polyketals, polyorthocarbonates, polyphosphazenes, polyhydroxyvalerates, polyalkylene succinates, poly(malic acid), polyorthoesters, and copolymers, block copolymers, branched copolymers and mixtures thereof.

9. The method of claim 1, wherein the at least one biodegradable polymer is selected from the group consisting of poly-D, L-Lactide (PDLLA), copolymers of lactide and glycolide (PLGA), copolymers of lactide and s-caprolactone, poly(lactide-ε-caprolactone) (PLA-ε-CL) copolyesters and polylactide-trimethylenecarbonate copolymer and amino acid-based polymers.

10. The method of claim 9, wherein the amino acid-based polymer is selected from the group consisting of tyrosine-based polyarylates and polycarbonates, leucine-based polyester urethanes, lysine-based polyester urethanes, polyesteramides, and mixtures thereof.

11. The method of claim 1, wherein the testosterone, dihydrotestosterone or an ester thereof is present in the formulation in an amount equivalent to 20 μg-2.5 mg of testosterone.

12. The method of claim 1, wherein the alendronate or salt thereof is present in the formulation in an amount of 1 μg-250 μg.

13. The method of claim 1, wherein said bone fracture or bone defect is a complicated fracture or a pathological fracture.

14. The method of claim 1, wherein the testosterone, dihydrotestosterone or an ester thereof is present in the formulation in an amount equivalent to 20 µg-5 mg of testosterone.

15. The method of claim 1, wherein the alendronate or salt thereof is present in the formulation in an amount of 0.5 µg-500 µg.

* * * * *